US007097846B2

(12) United States Patent
Wong et al.

(10) Patent No.: US 7,097,846 B2
(45) Date of Patent: Aug. 29, 2006

(54) 35 KD TUMOR ASSOCIATED PROTEIN ANTIGEN: USES AND METHODS OF DETECTION

(75) Inventors: Jan H. Wong, Los Angeles, CA (US); Rishab K. Gupta, Van Nuys, CA (US); Donald L. Morton, Pacific Palisades, CA (US)

(73) Assignee: CancerVax Corporation, Pacific Palisades, CA (US)

( * ) Notice: Subject to any disclaimer, the term of this patent is extended or adjusted under 35 U.S.C. 154(b) by 0 days.

(21) Appl. No.: 10/285,047

(22) Filed: Oct. 30, 2002

(65) Prior Publication Data

US 2003/0064065 A1 Apr. 3, 2003

Related U.S. Application Data

(60) Continuation of application No. 09/519,920, filed on Mar. 7, 2000, now Pat. No. 6,491,926, which is a division of application No. 08/422,644, filed on Apr. 14, 1995, now abandoned, which is a continuation of application No. 07/908,638, filed on Jul. 2, 1992, now abandoned, which is a continuation of application No. 07/510,602, filed on Apr. 18, 1990, now abandoned.

(51) Int. Cl.
*A61K 38/00* (2006.01)
(52) U.S. Cl. .............................. 424/277.1; 424/184.1; 424/130.1; 424/174.1; 530/387.1; 530/387.7
(58) Field of Classification Search ............ 424/184.1, 424/277.1, 130.1, 174.1; 530/387.1, 387.7
See application file for complete search history.

(56) References Cited

U.S. PATENT DOCUMENTS 4,851,510 A * 7/1989 Khan ..................... 530/388.85

OTHER PUBLICATIONS

Essell , J. NIH Res. 1995 7:46.*
Spitler, Cancer Biotherapy, 1995, 10:1-3.*
Boon, Adv. Can. Res. 1992 58:177-210.*

* cited by examiner

*Primary Examiner*—Sheela J. Huff
(74) *Attorney, Agent, or Firm*—Wilson, Sonsini, Goodrich & Rosati

(57) ABSTRACT

This invention provides the isolation and characterization of a tumor associated antigen which can be used for immunodiagnosis, immunoprognosis, and therapy of human cancer. The antigen is a protein molecule with a molecular weight of about 35 kD after reduction and separation by SDS-polyacrylamide gel electrophoresis. The antigen has been detected in serum of cancer patients.

4 Claims, 1 Drawing Sheet

35 KD TUMOR ASSOCIATED PROTEIN ANTIGEN: USES AND METHODS OF DETECTION

RELATED APPLICATIONS

This is a continuation application of application Ser. No. 09/519,920, filed Mar. 7, 2000, now U.S. Pat. No. 6,491,926; which is a divisional of Ser. No. 08/422,644, filed Apr. 14, 1995, abandoned; which is a continuation of application Ser. No. 07/908,638, filed Jul. 2, 1992, abandoned; which is a continuation of Ser. No. 07/510,602, filed Apr. 18, 1990, abandoned. Each of the foregoing is herein incorporated by reference in its entirety, including all drawings.

The present invention was made with support of grant numbers CA 30019, CA 12582 and CA 29605. The United States Government has rights in the invention.

BACKGROUND OF THE INVENTION

Various publications are cited throughout the application. Each of these publications are incorporated by reference into the application to more fully describe the invention.

It is well documented in animal models that cells, after neoplastic transformation in vivo, are changed biochemically and morphologically. In sufficient numbers, such transformed neoplastic cells are capable of inducing protective immunity against tumor development in syngeneic animals which are subsequently inoculated with viable cancer cells. This protective immunity was determined to be due to certain new cell components, called tumor specific transplantation antigens that were expressed by the neoplastic cells.

Expression of similar unique components by malignant cells is the fundamental hypothesis upon which tumor immunology is based. Substantial and convincing evidence now exist that clearly supports the concept that neoplastic transformation is associated with antigenic changes on the mammalian cell surfaces (Reisfeld R A and Cheresh D A: Ad Immunol 40:323–377,1987). To define a large group of cell surface antigens that appear to have, at least, increased expression on human tumor cells a variety of serologic strategies have been utilized (Old L J: Cancer Res 41:361–375,1981; Rosenberg S A, (ed.) Serologic Analysis of Human Cancer Antigens. Academic Press, New York. 1980.). The advent of hybridoma technology has provided highly specific and reproducible reagents for the study of cell surface antigens on human tumors.

The majority of antigens defined by monoclonal antibodies have proven to be glycoproteins (Liao S K, et al. Int J Cancer 30:573–580,1982., Loop S M, et al. Int J. Cancer 27:775–781,1981., Mitchell K F, et al. Proc Natl Acad Sci, USA, 77:7287–7291,1980,. Woodbury R G, et al. Proc Natl Acad Sci, USA. 77:2183–2187,1980). Utilizing murine monoclonal antibodies, a number of other melanoma associated antigens have been described (Mitchell K F, et al. Proc. Natl. Acad. Sci., USA, 77:7287–7291,1980: Woodbury R G, et al. Proc. Natl. Acad. Sci., USA. 77:2183–2187, 1980; Dippold W G, et al. Proc. Natl. Acad. Sci., USA 77:6114–6118,1980; Cheresh D A, et al. Proc. Natl. Acad. Sci., USA. 81:5767–5771,1984; Pukel C S, et al. J. Exp. Med., 155:1133–1147,1982; Yeh M Y, et al. Int. J. Cancer 29:269–275,1982). The majority of these antigens have been defined by cross reactivity in xenogeneic systems. It is apparent that murine monoclonal antibodies will most often define only strong species-specific antigens. Thus, subtle alterations in the tumor cell surface which most probably are critical to the unregulated growth of the malignant cell, may not be detected.

No evidence exists that antigens defined by murine monoclonal antibodies are immunogenic in the human host. Therefore, tumor associated antigens that are recognized as foreign and are immunogenic in man are of particular importance and may be critical both in the control of the cancer and as potential as diagnostic and or therapeutic reagents.

Tumor associated antigens that have been defined by autologous and allogeneic antibodies in human neoplasms can vary widely in their distributions. Some tumor associated antigens are expressed only by an individual tumor cell line or tumor. Others are shared by histologically similar tumors and still others by a variety of histologically distinct cancers including organs from which the tumor arose from and fetal tissues. Those antigens that are expressed only by an individual tumor are of limited importance for immunodiagnosis and treatment of cancer since tumor cell lines generally cannot be established from every tumor and cannot be applied to another patient. In contrast, tumor antigens that are shared by different tumors of the same histologic type or by histologically dissimilar tumors have potential application for immunodiagnosis, immunoprognosis and treatment of different patients with various types of malignancies.

There are well-documented instances which suggest that immunity against growing neoplasm in humans can be enhanced by active immunization with antigen-bearing tumor cells. The purpose of such active specific immunotherapy is to enhance the level of anti-tumor immunity beyond that which is naturally induced by the growing neoplasm. It is believed that a growing neoplasm does not induce a maximum immune response in the host to the tumor associated antigens it contains. Most immunotherapy attempts thus far have involved vaccines prepared from whole tumor cells, because progress has been slow in the isolation and purification of human tumor associated antigens. The possibility that living autologous tumor cells could result in tumor growth at the inoculation site has inhibited the use of such vaccines in man. However, tumor cells that express high levels of shared common tumor-associated antigens can be used to immunize different patients (Morton, D. L. et al, In Terry, W. D., Rosenberg, S. A. (eds): Immunotherapy of Human Cancer. New York, Elsevier North Holland, pp 245–249 (1982); Livingston P. O., et al., Int. J. Cancer 31:567 (1983)). The advantage of using such an allogeneic vaccine is two-fold: (1) an immune response induced against the foreign HLA transplantation antigens on the allogeneic vaccinated tumor cells would cause their rejection; (2) this immunization should induce a strong immune response against the shared common cross-reacting tumor-associated antigens to which the human leukocyte antigens (HLA) might serve as a helper function.

Approximately 40% of melanoma sera have been shown to contain antibodies to an antigen that was present in the partially purified spent culture medium of a melanoma cell line, (Gupta et al. JNCI 63:347–356 (1979)). The antigen was subsequently partially purified from the spent culture media of a melanoma cell line. Under nondissociating conditions, a gradient polyacrylamide gel electrophoresis (PAGE) analysis revealed that the antigen was a complex of about 450 kD which, by SDS (PAGE) analysis, under dissociating conditions, resolved into at least 5 bands that were stainable by Coomassie blue. One or two of these bands in the 60 to 70 kD range reacted with the antibody present in an allogeneic serum. This antigen, because of its cross reactivity with fetal tissues, was designated fetal antigen (FA) (Gupta R K and Morton D L: JNCI:70; 993–1003 (1983)). Prevalence of antibody to the antigen in cancer and non-cancer sera was frequent (56–88%). The antigen appeared to be widely expressed on melanoma, carcinoma, and sarcomas as well as on human fetal liver and brain but only infrequently on normal tissues obtained from non-cancer patients. Immunochemical characterization of the partially purified antigen preparation suggested the antigen to be a glycoprotein. The epitope recognized by human antisera was heat stabile and the immunoreactive part of the molecule was the carbohydrate portion of the antigenic complex molecule.

Obviously, the identification of additional tumor associated antigens is extremely important for diagnosis and treatment of cancers, particularly where the antigen is present on a large percentage of tumor cells but not normal cells. The present invention satisfies this need by providing a tumor-associated antigen. This antigen while discovered in conjunction with a study of FA represents a novel tumor-associated antigen.

SUMMARY OF THE INVENTION

This invention provides the isolation and characterization of a tumor associated antigen which can be used for immunodiagnosis, immunoprognosis, and therapy of human cancer. The antigen is a protein molecule with a molecular weight of about 35 kD. The antigen has been detected in serum of cancer patients.

DETAILED DESCRIPTION OF THE INVENTION

Figure 1:
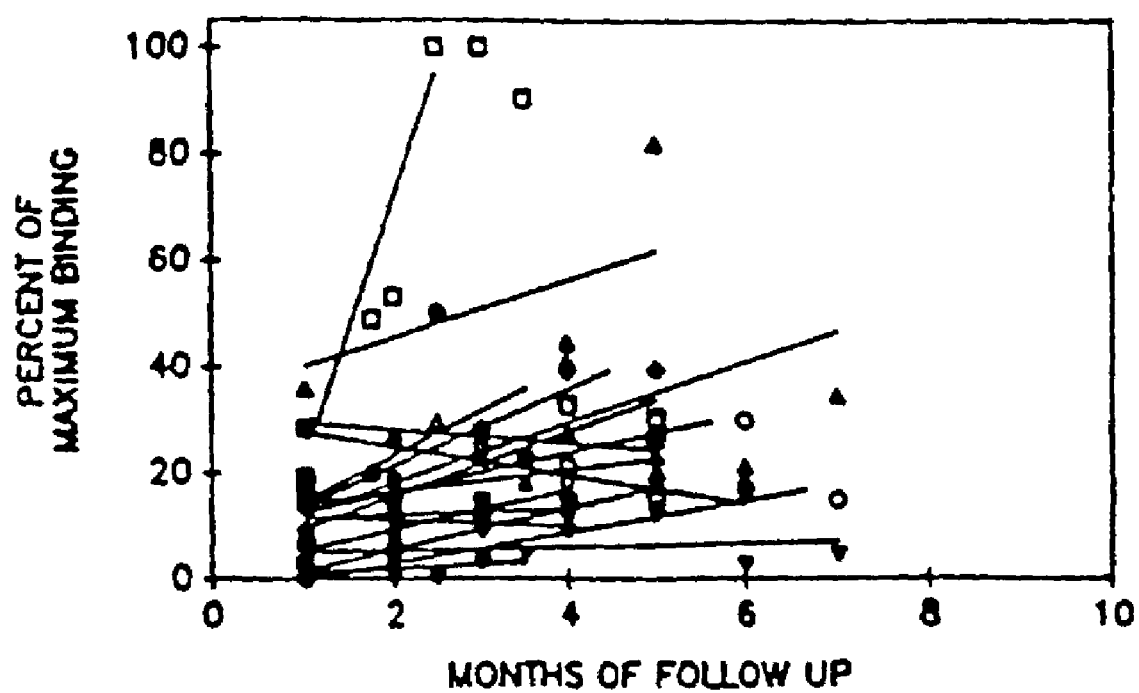
FIG. 1 shows a prospective analysis of an antigen specific IC. The lines represent 1st order linear regression of the serial analysis of melanoma patients and suggests increasing percent maximum binding in the majority of patients. Twenty-four patients have recurred. Eighteen of these patients have had elevated percent maximum binding prior to or at the time of the clinical recurrence.

As used-herein, "35 kD Protein" refers to a protein produced by tumor cells which may be present on the cell surfaces or in the culture medium of these cells as an aggregate with other molecules. The protein itself can be present in sera of cancer patients in the form of immune complexes. A murine monoclonal antibody, MAb, specifically recognizes an epitope on this molecule. This molecule may be found in other body fluids of cancer patients. The 35 kD protein also includes any modifications to the protein which do not change its essential immunologic character. Therefore, 35 kD protein includes immunogenic fragments of the protein.

As used herein "substantially purified" means substantially free of contaminants which are associated with the protein in its native environment.

As used herein "specifically binds" means the reagent binds the 35 kD protein with a sufficient affinity to detect the protein and distinguish it from other undesired proteins. An affinity of greater than about $10^6$ or $10^7$ is preferred.

The invention provides a novel 35 kD tumor associated antigen. The 35 kD protein has been separated from the majority of normal serum proteins by immunoaffinity chromatography, using the murine monoclonal antibody designated JSI (MAb JSI). Thus, the invention also provides a novel epitope recognized by MAb JSI. The murine monoclonal antibody was developed, using a partially purified fraction of spent culture medium of a melanoma cell line. This fraction contained the 60–70 kD fetal antigen (FA). On the basis of molecular size and the chemical nature of the epitope recognized by the MAb JSI on the 35 kD subunit and the FA, these two components are different. The difference is demonstrated by treatment of the 35 kD molecule with proteases which significantly eliminated its reactivity with the MAb JSI but did not effect the reactivity of FA. Thus, the reactive portion of the 35 kD molecule is a protein while the reactive portion of FA is a carbohydrate. However, treatment with B-galactosidase or hyaluronidase abolished the FA activity in the partially purified fraction of the spent culture medium.

By screening hybridoma supernatants against the immunizing material, partially purified fraction of spent culture medium of a melanoma cell line, it was possible to identify several antibody-producing clones with specificity for the tumor-associated protein. However, only one clone MAb JSI, has continued to produce the antibody. This MAb recognizes a protein epitope which occurs with a much greater frequency in the serum of cancer patients than in that of normal individuals or patients afflicted with autoimmune diseases. Therefore, the murine monoclonal antibody is useful for immunodiagnosis and immunoprognosis of human cancer.

The invention provides a substantially purified antigenic protein, produced by melanoma cells and present in circulation of cancer patients, which, after reduction and separation by SDS-polyacrylamide gel electrophoresis, has a molecular weight of about 35 kD. The protein is specifically bound by MAb JSI. The 35 kD protein has been detected in the sera of 75% of melanoma patients with recurrent disease, but rarely in the sera of apparently normal individuals (5%).

By contacting the 35 kD antigen from a body fluid of an afflicted subject with a reagent, the amount of the antigen, per a given amount of body fluid, can be compared with an amount previously determined for an equivalent sample; a variation in the antigen indicates a variation in the state of the malignancy. Thus, monitoring a malignancy refers to the process of repeatedly assaying an afflicted subject's body fluids to determine the amount of 35 kD protein present in the fluid.

Assays may be performed early in the treatment of the patient, as well as during and after treatment. Initially, 35 kD protein antigen levels may be very high, indicating a high turnover or shedding of the antigen. However, after treatment and inhibition of proliferation of tumor cells by vaccination, for example, the levels in a patient's body fluids may decrease.

The invention provides a method of detecting a cancer in a subject, comprising detecting the presence of 35 kD protein from a sample of the subject. The detection comprises binding the 35 kD protein antigen with a reagent and detecting the reagent. One example of detection is the binding of the 35 kD protein antigen directly or indirectly by a second reagent. The reagent is preferably an antibody but can be any suitable reagent.

A vaccine is provided for inducing or enhancing antibodies or cell-mediated immunity directed against the 35 kD protein comprising the 35 kD protein including immunogenic fragments thereof, and a pharmaceutically acceptable carrier. In addition, whole tumor cells having the 35 kD protein can be useful as a vaccine. The vaccine can induce or enhance, in a subject afflicted with a cancer, the production of antibodies reactive with the protein having a molecular weight of 35 kD. The method comprises administering to the subject an effective dose of the vaccine. The subject of the present invention is usually a human being; however, any animal may be used. The antibodies produced in the individual after administration of the vaccine inhibits, or treats, the cancer, for example, a melanoma. Inhibiting the cancer refers to the ability to contact the tumor cells with a reagent which can prevent the cells from proliferating, thus resulting in cell death and a reduction of the size of the tumor. Alternatively, inhibiting can include a direct cytotoxic effect on the tumor cells.

In addition, the invention provides methods of obtaining reagents which are reactive with antibodies which are reactive with the 35 kD protein Tumor Associated Antigen. These reagents can be anti-idiotype antibodies which bear the internal image of the antigen of interest. Idiotypes are antigenic determinants of the antibody combining site; therefore, anti-idiotype antibodies mimic the antigenic epitope of an antigen. The invention provides a method of immunotherapy comprising injecting into a subject a therapeutic amount of the anti-idiotypic antibody. The therapeutic amount is any amount effective to produce a cytostatic or cytotoxic effect on the tumor cells and can readily be determined by one skilled in the art.

The discovery that the 35 kD protein is associated with the tumor cell membrane indicates a method of treating a tumor expressing the antigen in a subject comprising injecting into the subject a tumor inhibiting reagent reactive with the 35 kD protein associated with the tumor cell membrane. The reagent can be an antibody or an antibody attached to a cytotoxic or cytostatic agent. The cytotoxic or cytostatic agent can, for example, be selected from the group consisting of toxins, radiolabeled moieties, and chemotherapeutic agent. The invention further provides a method of detecting the 35 kD protein on tumor cells such as obtained from a biopsy comprising contacting the tumor cells with a reagent specifically reactive therewith and detecting the bound reagent. Such detection can be effected by suitable means, well known to those skilled in the art.

A nucleic acid encoding the 35 kD protein and nucleic acid probes capable of selectively hybridizing with the encoding nucleic acid are also provided. The encoding nucleic acid can encode an antigenic portion on the 35 kD protein. In addition, the nucleic acid can correspond to an antigenic sequence on an anti-idiotypic antibody.

A method of in vivo detection of a tumor in a subject is also provided. The method comprises injecting into the subject, a reagent, for example, an antibody, reactive with the 35 kD protein on the tumor cell surface, detecting the presence of the reagent which reacts with the 35 kD protein and thereby detecting the tumor. The tumor may be, for example, a melanoma, sarcoma, or carcinoma.

Still further the invention provides a method for detecting low levels of the 35 kD protein, comprising enhancing the expression of the protein in cancer cells with alpha- or gamma-interferon, or other biological response modifiers, e.g., retinoic acid, contacting the 35 kD protein with a reagent specifically reactive therewith and detecting the presence of the reagent. The use of interferon as an anticancer agent is currently under intensive investigation. Gamma interferon is produced when sensitized lymphocytes are stimulated with specific antigens. Interferon can be administered to a subject by injection. Gamma interferon has been shown to induce, enhance or inhibit the expression of several genes. Among those induced are HLA genes including A, B, and C. The expression of HLA genes allows certain cells to be more easily recognized and cleared by the immune system.

The following examples are intended to illustrate, but not to limit, the invention:

EXAMPLE I

Development of Murine Monoclonal Antibody

The antigenic fraction was partially purified from the spent culture medium of a melanoma cell line, UCLA-SO-M14 (M14) which had been adapted to grow in a chemically defined serum free medium. Details of the collection and preparation of the spent culture medium have previously been described (Gupta, R. K. and Morton D. L., JNCI 70:993–1003 (1983)). Briefly, the spent culture medium was concentrated and ultrafiltered through a membrane with an exclusion limit of 100 Kd. The material retained on the membrane was chromatographed on a Sepharose 6B column and the antigen fraction was extracted with chloroform: methanol (2:1). The aqueous phase material contained FA and other protein components.

Six week old female BALB/c mice were immunized intraperitoneally on day 1, day 8 and day 20 with 100 µl of the partially purified antigen fraction (6 µg/ml) that had been isolated and partially purified as previously described. Seven days following the final immunization the mice were splenectomized. The sensitized splenocytes were mixed with SP2/0 murine myeloma cells (American Type Culture Collection, Rockville, Md.) in a ratio of 7:1 (lymphocytes: myeloma) and fused in 40% polyethylene glycol 1500 as described by Oi and Herzenberg (Oi and Herzenberg, In Selective Matters in Cell Immunology, Ed. D. B. Mishell and S. M. Shiji, p. 351–372, (1980)). The fused cells were transferred to 96-well microculture plates at a concentration of $5\times10^5$ cells/well and cultured for 2 weeks in HAT (hypoxanthine, aminopterin, thymidine) media to select lymphocyte-myeloma hybrid cells. At confluence the hybridomas were screened for the presence of antibody to the partially purified antigen preparation. Hybridomas that screened positive for the presence of antibody to the partially purified antigen preparation were cloned at least four times by the limiting dilution method and mass produced in pristine primed mice. The antibody subtype was determined by immunodiffusion on commercially prepared plates (Kallestad Laboratories, Chaska, Minn.).

EXAMPLE II

Application of JSI Monoclonal Antibody to Detect 35 kD Protein Containing Immune Complexes The technique developed by Engvall and Perlmann (Engvall and Perlmann, J. Immunol. 109:129–135, (1972)) was adapted to detect antigen specific circulating immune complexes in human sera. MAb JSI (5–10 mg/ml) was obtained from the ascites of pristine primed mice and partially purified by precipitation with 60% $(NH_4)_2SO_4$. The mouse hybridoma cell line which produces MAB JSI was deposited on Mar. 14. 2002 and was given accession number PTA-4136 by the American Type Culture Collection ("ATCC"). 10801 University Blvd. Manassas, Va. 20110–2209. Ninety-six well Immulon microtitration plates (Dynatech Laboratories, Alexandria, Va.) were sensitized with 100 µl (50–100 µg/ml) of the partially purified MAb JSI ascites fluid that was diluted 100 fold in 0.06 M carbonate buffer (pH 9.6) and incubated at 4° C. for 16 hours prior to use. The wells were emptied and washed three times with 0.25 M sodium phosphate buffer supplemented with 0.15 M NaCl and 0.05% Tween 20 (PBS/T) and blocked with 100 µl of a 1% solution of bovine serum albumin (Sigma Corp., St. Louis, Mo.) in PBS/T for 10 minutes at 26° C. Sera (100 µl at a dilution of 1:200) was dispensed into the wells and incubated at 37° C. for 1 hour. All samples were run in triplicate. In order to minimize the possibility of cross reactivity with the immobilized mouse Ig, the serum was diluted with a 1% solution of mouse serum. Binding of human Ig containing immune complexes by the immobilized monoclonal antibody was detected with a 1:400 diluted goat anti-human IgG antibody conjugated to alkaline phosphatase (Sigma Corp., St. Louis, Mo.) with p-nitrophenyl phosphate (1 mg/ml) in 10% diethanolamine buffer (pH 9.8) as the substrate. The color developed in each well after incubation at room temperature and was read at 405 mm in a Multiscan (Flow Laboratories, Inglewood, Calif.) and compared with a positive control serum that had developed an OD reading of approximately 1.0. Results were expressed as percent of maximum binding and was calculated as follows: Percent Maximum Binding= $(OD_{salute}-OD_{NSB}/OD_{NSB})\times 100$ where NSB=non specific background binding. A logistic regression analysis was performed to determine a cutoff percent maximum binding to distinguish sera obtained from melanoma patients and other populations of individuals. We determined by studying normal serum and sera from melanoma patients that a percent maximum binding of >15.5% to be positive for the presence of antigen specific IC.

Interassay Variability

The interassay variability and reproducibility of the sandwich assay was determined by testing 9 serum samples from melanoma patients with various levels of binding to the monoclonal antibody. These samples were aliquoted and frozen and then studied on three separate occasions. Additionally, the 9 serum samples were studied following freezing and thawing. The selected serum samples were tested on 5 different polystyrene plates on three separate occasions. Because of the skewed distribution, a natural log transformation of the percent maximum binding was utilized to conduct an analysis of variance (ANOVA). Table 1 summarizes the results of these assays. The values represent the mean of the natural log transformation of the percent of maximum binding. By ANOVA analysis, no additive effect on the results obtained were noted by either the plate utilized or the time the assay was performed (p=0.99) or by the plate utilized (p=0.97) or the time the assay was performed alone (p=0.34). Although some variability was noted between results, particularly over time, when 15.5% binding was considered positive for the presence of antigen specific immune complexes, the concordance of these reactions within one standard deviation of the mean of the percent of maximum binding was 89% (8/9 serum samples).

Table 1

ANOVA analysis of Interassay variation to determine the effect of the ELISA plate utilized in the sandwich assay and the time the assay was performed on results. The values represent the mean of the natural log of the percent maximum binding of all samples tested on a given day and on a given plate. There is no significant effect on results by either the plate utilized or time the assay was performed.

| Plate | DAY | | | TOTAL |
| --- | --- | --- | --- | --- |
| | 1 | 2 | 3 | |
| 1 | 2.44 | 2.51 | 2.96 | 2.55 |
| 2 | 2.68 | 2.34 | 2.87 | 2.63 |
| 3 | 2.56 | 2.70 | 2.87 | 2.71 |
| 4 | 2.63 | 2.58 | 2.77 | 2.66 |
| 5 | 2.43 | 2.52 | 2.76 | 2.58 |
| Total | 2.55 | 2.53 | 2.79 | 2.62 |

Additive effect of day and plate (p=0.9991) Plate effect without consideration of day effect (p=0.9727) Day effect without consideration of plate effect (p=0.3409)

EXAMPLE III

Purification and Characterization of the 35 kD Protein from Serum of a Melanoma Patient An immunoaffinity column (1.5×15 cm) was prepared with the partially purified ammonium sulfate precipitated MAb JSI. MAb JSI (50 mg) was oxidized with sodium m-periodate (NaIO$_4$) for one hour at room temperature. Immediately after the 1-hour oxidation, the sodium periodate was removed from the IgG solution by passage over an Econo-Pac 10 DG desalting column (Bio-Rad, Richmond, Calif.). Following desalting, the oxidized MAb was added to Affi-gel Hz Hydrazide gel (25 ml) (Bio-Rad, Richmond, Calif.) and coupled by rotating end-over-end for 24 hours at room temperature in a coupling buffer (10 mM NaAcetate, 150 mM NaCl, pH 5.5). Following coupling, the gel was packed and washed with 0.1 M phosphate buffered saline (PBS, 0.5 M NaCl). Three ml of patient serum that had been shown to be positive in the sandwich ELISA for antigen specific circulating immune complexes was applied to the column at room temperature. The column was washed with PBS (pH 7.2) until the eluate decreased below 0.05 at 280 nm. Antigen specific immune complexes were eluted with an acid buffer (0.2 M glycine-HCl pH 2.5, 0.1 M-acetic acid, 0.15 M sodium citrate, pH 3.0, 0.5 M formic acid). The fractions were then studied at pH 3.0 and following neutralization with 1 M Tris.Cl, pH 9.0. Each fraction was analyzed for the presence of antigen specific immune complexes in the sandwich ELISA at both pH 3.0 and pH 8.0. The antigenic activity was confined to the elution volume. This material was further utilized to determine biochemical properties of the antigen.

Treatment of Affinity Isolated Antigen from Serum by Enzymes and Heat

Trypsin and protease immobilized on-agarose beads were obtained (Sigma Corp., St. Louis, Mo.) and prepared per protocol. A 500 µl (150 µg protein) aliquot of affinity isolated antigen was exposed to the enzymes (1 unit) and mixed by rotating end-over-end for one hour at 4° C. We utilized cyanogen bromide agarose beads that had been blocked with diethanolamine as a control and mixed them with an identical volume of affinity isolated antigen. The mixture was centrifuged at 7000×g for 10 minutes and the supernatant containing the trypsin and protease treated antigen was utilized to sensitize 96 well Immulon polystyrene plates (Dynatech Laboratories, Richmond, Va.) for use in a standard enzyme linked immunosorbent assay. Reactivity with the monoclonal antibody was determined utilizing goat anti-mouse IgG conjugated to alkaline phosphatase.

EXAMPLE IV

Isolation of 35 kD Protein from Melanoma Cell Membrane, Membrane Lysate Preparation Melanoma cells (M14) were grown in RPMI 1640 supplemented with 10% fetal calf serum as previously described. The cells were harvested by agitation and stored packed at −40° C. until utilized. The frozen cells were thawed and suspended in ice cold Tris/saline/azide (TSA) buffer (0.002 M Tris.Cl, pH 8.0, 0.14 M NaCl, 0.025% $NaN_3$ 0.5% Triton X-100, 0.5% sodium deoxycholate) in a 1:5 volume packed cells to TSA. An equal volume of cold lysis buffer (2% Triton X-100, 5 mM iodoacetamide, 1 mM phenylmethylsulfony fluoride in TSA) was added to the cells in 1:1 volume to volume ratio. The mixture was rotated, end-over-end, for one hour at 4° C. The mixture was centrifuged at 4000×g for 10 minutes and the supernatant decanted. The membrane antigens were purified with the addition of 5% sodium deoxycholate and then centrifuged at 150,000×g for two hours. The supernatant was collected and stored at 4° C. until utilized for study.

Affinity Isolation of Antigen from Membrane Lysate

An affinity column was prepared as previously described and washed with 10 column volumes wash buffer (0.1 M Tris.Cl, 0.14 M NaCl, 0.025% $NaN_3$, pH 8.0) and subsequently 5 column volumes each of Tris buffer at pH 8.0 and at pH 9.0 and triethanolamine solution (50 mM triethanolamine, 0.1% Triton X-100, 0.5 M NaCl). The membrane lysate was applied to the column and successively eluted with 10 column volumes of wash buffer, 5 column volumes each of Tris buffer (pH 8.0) and 5 column volumes of Tris buffer (pH 9.0). The antigen was eluted with triethanolamine solution and collected into fractions containing 1 M tris.Cl, pH 6.7 to neutralize the fractions.

Polyacrylamide Gel Electrophoresis

The method of Laemmli, U. K., Nature 227:680–685 (1970), was employed to isolate the antigen and to determine the monoclonality of MAb JSI. Briefly, the protein was solubilized in the presence of 1% sodium dodecyl sulfate (SDS), heated for one minute at 100° C. in the presence of 2-mercaptoethanol and applied to the 12% polyacrylamide gel in a Protean II minigel electrophoresis apparatus (Bio-Rad, Richmond, Calif.). The gel was run at 200 volts until the tracking dye traversed the gel. The presence of protein was determined by staining with Coomaisse Blue. The bands were excised and finely minced. The antigen was extracted from the gel fragments by resuspending them in phosphate buffered saline (0.5 M NaCl PBS). The mixture was centrifuged at 10,000×g for 10 minutes to remove the gel fragments and the supernatant utilized to sensitize 96 well Immulon microtiter plates. Reactivity with MAb JSI was determined in a standard ELISA as previously described above utilizing goat anti-mouse IgG conjugated to alkaline phosphatase. Reactivity was limited to the band in the region of 35 kD.

EXAMPLE V

Analysis of Sequential Serum Samples of Melanoma Patients

The availability of an extensive serum bank allowed the serial study of a number of patients for the presence of antigen specific IC as determined in the sandwich assay. FIG. 1 summarizes these results. There is clearly an elevation of antigen specific IC in patients who had recurrent disease. In contrast, patients who were negative for the presence of antigen specific IC with recurrent melanoma, never manifested antigen specific IC. Because the assay detects IC, these levels are not only influenced by the presence of antigen but also by the presence of antibody and clearance of the IC from circulation. Thus, quantitation of the antigen level by frequent intervals provides an improved marker. Of interest is the fact that although several of these patients were apparently rendered clinically free of tumor, the antigen specific IC levels remained elevated throughout their post operative course. Studies demonstrate that approximately 75% of patients who develop recurrent melanoma will be positive for the presence of antigen specific IC at or before the time of the clinical recurrence.

Although the invention has been described with reference to the presently preferred embodiment, it should be understood that various modifications can be made without departing from the spirit of the invention. Accordingly, the invention is limited only by the claims.

What is claimed:

1. A composition comprising a 35 kD protein or fragment thereof having an epitope that is specifically bound by monoclonal antibody JSI, deposited under ATCC designation number PTA-4136, and a pharmaceutically acceptable carrier.

2. The composition of claim 1 wherein said 35 kD protein or fragment thereof is substantially purified.

3. A composition comprising an anti-idiotypic antibody derived from the epitope on a 35 kD protein that is specifically bound by monoclonal antibody JSI, deposited under ATCC designation number PTA-4136, and a pharmaceutically acceptable carrier.

4. The composition of claim 1, wherein said composition comprises cells comprising said 35 kD protein or a fragment thereof.

* * * * *

UNITED STATES PATENT AND TRADEMARK OFFICE
Certificate

Patent No. 7,097,846 B2

Patented: August 29, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Donald L. Morton, Pacific Palisades, CA (US).

Signed and Sealed this Sixteenth Day of October 2007.

LARRY HELMS
*Supervisory Patent Examiner*
Art Unit 1643